(12) United States Patent
Packer et al.

(10) Patent No.: US 9,675,470 B2
(45) Date of Patent: Jun. 13, 2017

(54) LATERALLY EXPANDABLE SPINAL PROSTHESIS

(71) Applicant: P&H Medical Products, LLC, Delray Beach, FL (US)

(72) Inventors: Evan Packer, Boca Raton, FL (US); James Scott Hay, Parkland, FL (US)

(73) Assignee: P&H Medical Products, LLC, Delray Beach, FL (US)

( * ) Notice: Subject to any disclaimer, the term of this patent is extended or adjusted under 35 U.S.C. 154(b) by 0 days.

(21) Appl. No.: 15/232,965

(22) Filed: Aug. 10, 2016

(65) Prior Publication Data

US 2016/0354211 A1 Dec. 8, 2016

Related U.S. Application Data

(63) Continuation-in-part of application No. 13/656,256, filed on Oct. 19, 2012, now Pat. No. 9,439,771.

(Continued)

(51) Int. Cl.
*A61F 2/44* (2006.01)
*A61F 2/46* (2006.01)
(Continued)

(52) U.S. Cl.
CPC .............. *A61F 2/447* (2013.01); *A61F 2/442* (2013.01); *A61F 2/4611* (2013.01); *A61F 2002/2817* (2013.01); *A61F 2002/2835* (2013.01); *A61F 2002/3085* (2013.01); *A61F 2002/30393* (2013.01); *A61F 2002/30401* (2013.01); *A61F 2002/30405* (2013.01); *A61F 2002/30418* (2013.01); *A61F 2002/30476* (2013.01); *A61F 2002/30507* (2013.01); *A61F 2002/30523* (2013.01); *A61F 2002/30525* (2013.01); *A61F 2002/30556* (2013.01);
(Continued)

(58) Field of Classification Search
CPC .... A61F 2/4425; A61F 2/447; A61F 2/30523; A61F 2/30525
See application file for complete search history.

(56) References Cited

U.S. PATENT DOCUMENTS 8,357,181 B2 * 1/2013 Lange ................ A61B 17/7065
606/248
8,409,285 B2 * 4/2013 Keller ...................... A61F 2/44
623/17.11

(Continued)

*Primary Examiner* — David Bates
*Assistant Examiner* — Olivia C Chang
(74) *Attorney, Agent, or Firm* — Nicholas R. Lewis

(57) ABSTRACT

An expandable spinal prosthesis is disclosed, including a first surface having a first plurality of tissue anchors; a second surface opposite the first surface, the second surface having a second plurality of tissue anchors; a first wall between the first and second surfaces, and a second wall between the first and second surfaces, the second wall located opposite the first wall and being movable with respect to the first wall. A surgical instrument is also provided, including an elongated shaft defining a proximal end and a distal end; a first prosthesis engagement element accessible from the proximal end and extending from the distal end; and a second prosthesis engagement element accessible from the proximal end and extending from the distal end, the second prosthesis engagement element including a plurality of gear teeth.

20 Claims, 7 Drawing Sheets

Related U.S. Application Data

(60) Provisional application No. 61/548,819, filed on Oct. 19, 2011.

(51) Int. Cl.
*A61F 2/28* (2006.01)
*A61F 2/30* (2006.01)

(52) U.S. Cl.
CPC ............... *A61F 2002/30601* (2013.01); *A61F 2002/30904* (2013.01); *A61F 2002/4475* (2013.01); *A61F 2002/4615* (2013.01); *A61F 2002/4628* (2013.01); *A61F 2002/4629* (2013.01)

(56) References Cited

U.S. PATENT DOCUMENTS

| | | | | |
|---|---|---|---|---|
| 8,721,723 B2* | 5/2014 | Hansell | ..................... | A61F 2/44 623/17.15 |
| 8,801,788 B2* | 8/2014 | Merves | ..................... | A61F 2/44 606/279 |
| 2014/0207236 A1* | 7/2014 | Prevost | ..................... | A61F 2/44 623/17.16 |

\* cited by examiner

LATERALLY EXPANDABLE SPINAL PROSTHESIS

CROSS-REFERENCE TO RELATED APPLICATION

This application is a continuation-in-part-of patent application Ser. No. 13/656,256, filed Oct. 19, 2012, entitled LATERALLY EXPANDABLE SPINAL PROSTHESIS, which is related to and claims priority from Provisional Patent Application Ser. No. 61/548,819, filed on Oct. 19, 2011, the entirety of all of which is incorporated herein by reference.

STATEMENT REGARDING FEDERALLY SPONSORED RESEARCH OR DEVELOPMENT n/a

FIELD OF THE INVENTION

The present invention relates to spinal prostheses and orthopedic instrumentation and methods of use thereof.

BACKGROUND OF THE INVENTION

When healthy, intervertebral discs located between endplates of adjacent vertebrae stabilize the spine and distribute forces between the vertebrae and cushion vertebral bodies. However, the spinal discs may be displaced, damaged, or degraded due to trauma, disease or aging. A herniated or ruptured annulus fibrosis may result in nerve damage, pain, numbness, muscle weakness, and even paralysis. Furthermore, as a result of the normal aging processes, discs dehydrate and harden, thereby reducing the disc space height and producing instability of the spine and decreased mobility.

In many instances, one or more damaged structural body parts can be repaired or replaced with a prosthesis or implant. For example, typical surgical correction of a collapsed disc space includes a surgical removal of the damaged vertebra (in whole or in part) and/or the damaged disc (in whole or in part) followed by the insertion of an implant or prosthesis. In some cases, it is necessary to stabilize a weakened or damaged spinal region by reducing or inhibiting mobility in the area to avoid further progression of the damage and/or to reduce or alleviate pain caused by the damage or injury. In other cases, it is desirable to join together the damaged vertebrae and/or induce healing of the vertebrae. Accordingly, an implant or prosthesis may be configured to facilitate fusion between two adjacent vertebrae. The implant or prosthesis may be placed without attachment means or fastened in position between adjacent structural body parts (e.g., adjacent vertebral bodies).

Access to a damaged disc space may be accomplished from several approaches to the spine. One approach is to gain access to the anterior portion of the spine through a patient's abdomen. However, extensive vessel retraction is often required and many vertebral levels are not readily accessible from this approach. A posterior approach may also be utilized, but this typically requires that both sides of the disc space on either side of the spinal cord be surgically exposed. This may require a substantial incision or multiple access locations, as well as extensive retraction of the spinal cord.

To alleviate problems associated with both anterior and posterior approaches to the spine, a lateral approach to the disc space may be utilized. A lateral approach is a minimally-invasive surgical approach providing such benefits including minimal tissue damage and blood loss, smaller incisions and resulting scars, reduced post-operative discomfort, and reduced time needed for recovery. However, difficulties remain in placing prostheses of sufficient size to stabilize the spinal segment while also adhering to or otherwise allowing reduced incisions for surgical access to the tissue site. Moreover, the minimal size of the access can hamper accurate positioning of the prosthesis once inside the intervertebral space. Even further, due to variations in patient and/or intervertebral cavity sizes, it is often necessary to employ a range of differently-sized prosthesis that may need to be tried before selecting the best fit for a particular patient.

Accordingly, it is desirable to provide an implant that can be easily inserted in accordance with a specific pathway or approach, such as a lateral approach, and that further eases obtaining a desired prosthesis position and resulting spinal segment stabilization.

SUMMARY OF THE INVENTION

The present disclosure provides an expandable spinal prosthesis, including a first surface having a first plurality of tissue anchors; a second surface opposite the first surface, the second surface having a second plurality of tissue anchors; a first wall between the first and second surfaces, and a second wall between the first and second surfaces, the second wall located opposite the first wall and being movable with respect to the first wall. The expandable spinal prosthesis may include a first portion and a second portion, wherein the first portion defines the first wall and the second portion defines the second wall. The first portion may include a first surgical instrument engagement feature, such as a threaded surface. The first portion may include a second surgical instrument engagement feature, and the second portion may include a plurality of gear teeth accessible through the second surgical instrument engagement feature. The prosthesis may include a locking element positionable through the second surgical instrument engagement feature and engageable with the plurality of gear teeth to prevent movement between the first and second portions. The second portion may be securable in a plurality of discrete positions with respect to the first portion. The second portion may define a plurality of apertures alignable with an aperture in the first portion. The first and second portions may define a cavity therebetween. The expandable spinal prosthesis may include a radiopaque marker coupled to at least one of the first and second portions.

The present disclosure also provides a surgical instrument, including an elongated shaft defining a proximal end and a distal end; a first prosthesis engagement element accessible from the proximal end and extending from the distal end; and a second prosthesis engagement element accessible from the proximal end and extending from the distal end, the second prosthesis engagement element including a plurality of gear teeth. The first prosthesis engagement element may include a threaded shaft. The instrument may include a third prosthesis engagement element accessible from the proximal end and extending from the distal end, where the third prosthesis engagement feature is movable form a first position to a second position, and is biased to stay in the first position. The third prosthesis engagement element may include a rod adjustably extendable from the distal end. The surgical instrument may include a prosthesis locking element positioned within the shaft coaxial to the second prosthesis engagement element.

A method of implanting a spinal prosthesis within a patient is provided, including positioning a spinal prosthesis within an intervertebral space, the spinal prosthesis including a first portion and a second portion movably coupled to the first portion; and moving the second portion in a substantially posterior direction away from the first portion to increase a width of the prosthesis in an anterior-posterior direction. The method may include securing the position of the second portion relative to the first portion. Moving the second portion in a substantially posterior direction may be accomplished at least in part by mechanically actuating a gear interface of the prosthesis. The method may include introducing a biologic material into a cavity defined by the prosthesis. Positioning the spinal prosthesis may include directing the prosthesis into the intervertebral space in a substantially lateral-to-medial direction.

The present disclosure also provides an expandable spinal prosthesis, including a first surface and a second surface opposite the first surface, and a prosthesis height defined therebetween; a first wall extending between the first and second surfaces; a second wall extending between the first and second surfaces, the second wall located opposite the first wall; a first sidewall extending from the first wall to the second wall, wherein the first sidewall defines an opening therethrough; and a second sidewall extending from the first wall to the second wall, wherein the first wall, first sidewall and second sidewall form a unitary first portion; wherein at least a portion of the second wall forms a second portion movable relative to the first portion to extend an overall width of the prosthesis body; and wherein the second portion includes a first plurality of gear teeth and a second plurality of gear teeth positioned out-of-phase with respect to the first plurality of gear teeth, and wherein the first and second pluralities of gear teeth are accessible through the opening in the first sidewall.

The position of the second portion may be configured to be adjusted relative to the first portion using an external tool engaged with the first and second pluralities of gear teeth. The second portion may be securable in a plurality of discrete positions with respect to the first portion. The expandable spinal prosthesis may include a displacement indicator coupled to at least one of the first and second portions, where the displacement indicator provides at least one of a tactile and audible response to the movement of the second portion relative to the first portion. The displacement indicator may include a protruding segment coupled to the first portion that is engageable with a plurality of depressions defined by the second portion. The second portion may include or define at least one strain relief allowing the second portion to flex. The at least one strain relief may include a curvilinear recess in at least one of the first and second surfaces.

The expandable spinal prosthesis may include a locking element positionable through the opening in the first sidewall and engageable with the first and second pluralities of gear teeth to prevent movement between the first and second portions. The locking element may include a retention feature configured to resist movement of the locking element with respect to the first portion of the prosthesis. The retention feature may include a multi-prong clip configured to releasably engage an aperture defined by the second sidewall.

The first and second portions of the prosthesis may define a cavity therebetween, the cavity extending through the height of the prosthesis from the first surface to the second surface. The cavity may define a substantially rectangular-shaped cross section. The expandable spinal prosthesis may include one or more radiopaque markers coupled to at least one of the first and second portions. The first sidewall may define a first surgical instrument engagement feature, and the second sidewall may define an aperture coaxial with the first surgical instrument engagement feature. The first surgical instrument engagement feature may include a threaded surface.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention provides a prosthesis that can be easily inserted in accordance with a specific pathway or approach, such as a lateral approach, and that further eases obtaining a desired prosthesis position and resulting spinal segment stabilization. In particular, the prosthesis disclosed herein provides an adjustable, dynamic aspect ratio (i.e., the ratio of the width of the implant to its height) that can be adjusted to suit a varying range of surgical sites of different sizes in different patients. The adjustable size further allows a reduced, minimal profile during insertion while also allowing for expansion once positioned in a surgical site that may provide sufficient support and stabilization to negate a need for any additional posterior or anterior fusion hardware.

Figure 1:
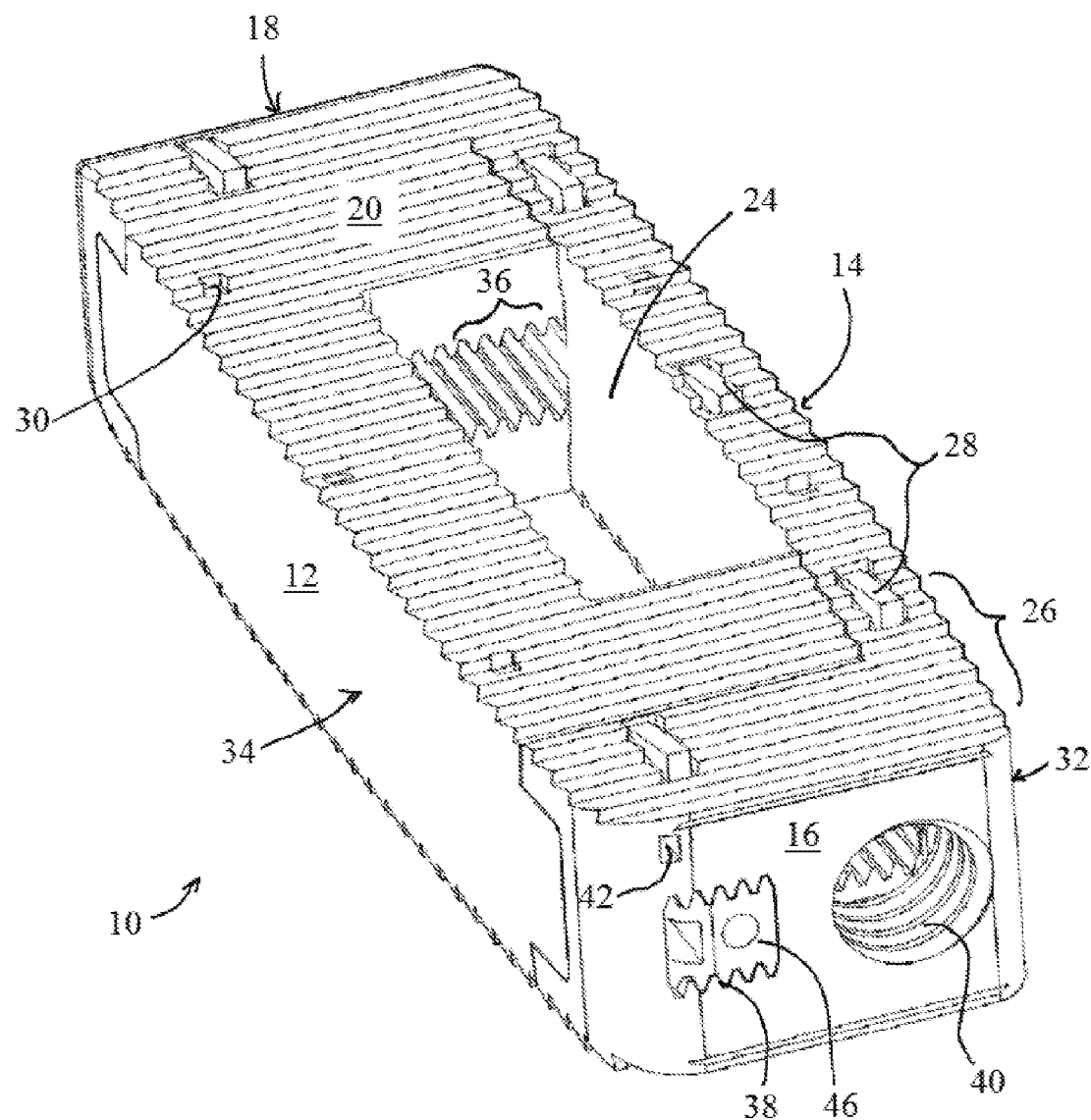
FIG. 1 is a perspective view of an example of an un-deployed or collapsed spinal prosthesis in accordance with the present disclosure.
Figure 2:
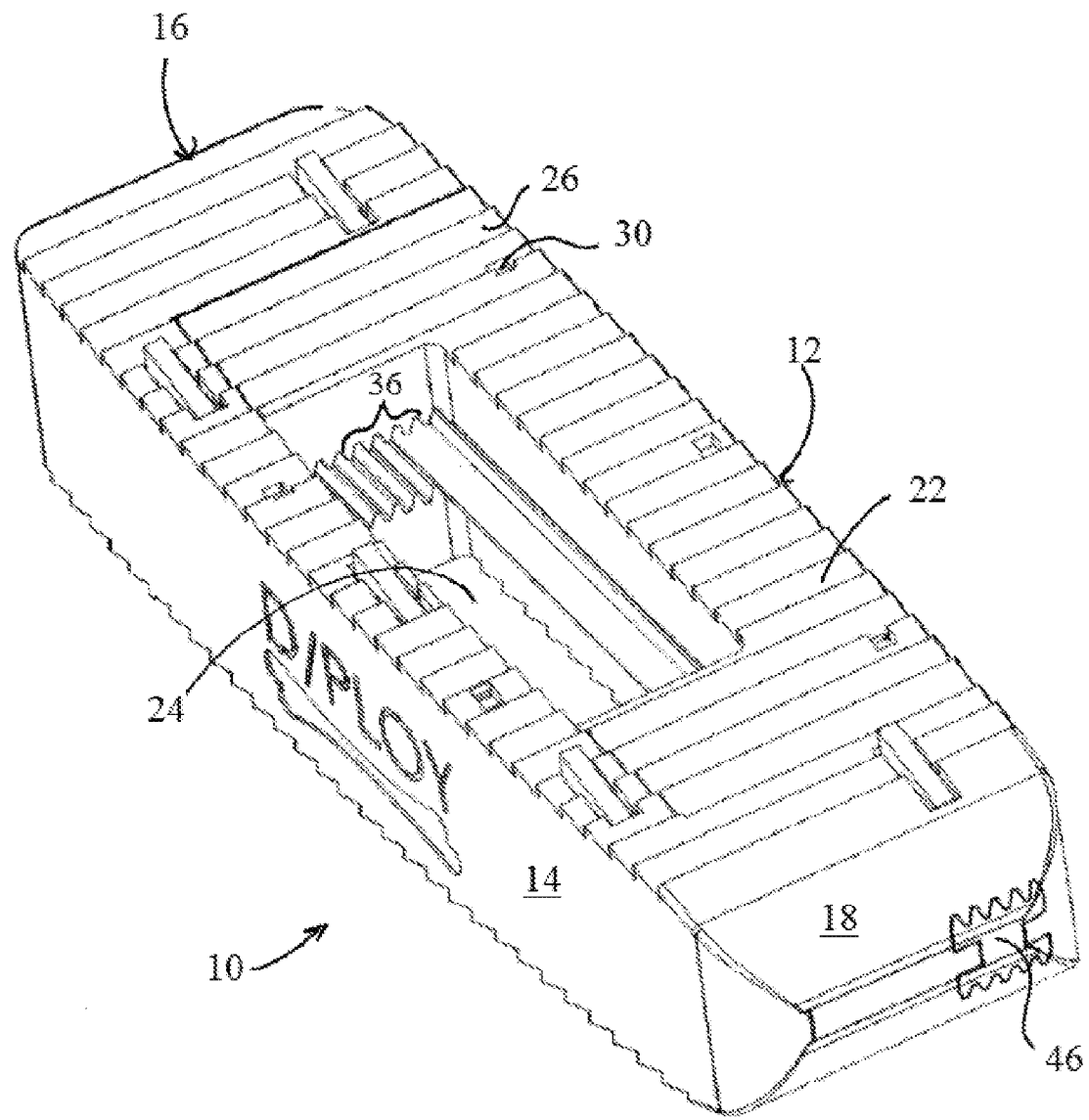
FIG. 2 is an additional perspective view of the prosthesis of FIG. 1.

Now referring to FIGS. 1-2, a spinal prosthesis 10 is provided, where the spinal prosthesis 10 may include a prosthesis body generally defining a posterior wall 12, an anterior wall 14, a proximal sidewall 16 and distal sidewall 18 extending from the posterior wall 12 to the anterior wall 14. The distal sidewall 18 may define a curved or "bull nose" profile to ease insertion into an intervertebral space. The spinal prostheses described herein may be constructed from a myriad of biocompatible materials, such as PEEK, for example, providing desired mechanical behavior throughout the range of movement and resultant forces experienced in a spinal column.

The spinal prosthesis 10 may further define an upper or cranial surface 20 and a lower or caudal surface 22. In addition, a cavity 24 may extend through a portion of the prosthesis 10 from the upper surface 20 to the lower surface 22, where the cavity 24 may provide a region for bone growth and/or the addition of filler or therapeutic materials to aid recovery and integration of the prosthesis into the surrounding tissue structure. The spinal prosthesis 10 may include a first plurality of tissue anchors or teeth 26 on at least a portion of the cranial and/or caudal surfaces 20, 22 to resist movement of the prosthesis 10 once implanted into the desired position. The teeth 26 may be sized or dimensioned to provide sufficient friction against movement of the implant upon implantation while reducing the likelihood that the teeth extend too far into the endplates of the surrounding vertebral bodies as to cause tissue damage. Each tooth or protrusion may generally define a base and a peak, and may further extend in an anterior-posterior direction between the anterior and posterior walls 12, 14 (i.e., the teeth 26 are "pointed" towards or resist movement in a proximal direction). The orientation of the teeth 26 thus aid in precluding or at least reducing movement of the prosthesis 10 in a medial-to-lateral anatomical direction once the prosthesis is placed into its final desired position. The prosthesis 10 may also include a second plurality of tissue anchors or teeth 28 positioned on at least a portion of the cranial and/or caudal surfaces 20, 22. The teeth 28 may be oriented longitudinally in the lateral direction and may include substantially rectangular geometry with large radii on the edges to preclude "snagging" tissue when the prosthesis 10 is being inserted. The teeth 28 may resist or preclude movement of the prosthesis in the anterior-posterior direction for safe expansion of the prosthesis 10, as discussed below.

The prosthesis may further include a plurality of radiopaque/radiographic markers 30 disposed about one or more surfaces or walls of the prosthesis 10. The markers 30 may be used to identify the position and orientation of the prosthesis during implantation through the use of fluoroscopic or other medical imaging means. The prosthesis 10 may also include one or more sensors or other informational components (not shown) that provide information regarding the loads experienced by the prosthesis 10, rates of fusion, biological assessment, etc. For example, a strain gauge (not shown) may be coupled to one or more walls or surfaces of the prosthesis, and RFID or other passive component may also be coupled to the prosthesis to facilitate information collection and transmission regarding a particular status or characteristic of the prosthesis 10.

As described above, the prosthesis 10 includes an adjustable, dynamic aspect ratio (e.g., height to width). In particular, the prosthesis includes a selectively adjustable expansion or deployment mechanism providing the ability for a single prosthesis to be used in a wide range of surgical site sizes, and thus patients. For example, the prosthesis 10 may generally include a first portion and a second portion movably coupled to the first portion. The first portion may include or define the anterior wall 14, the proximal sidewall 16, and/or the distal sidewall 18. The second portion may include or define the posterior wall 12, or a portion thereof. The first and second portions may each include or define at least part of the cranial and caudal surfaces 20, 22. The second portion 34 may be movable away from the first portion to extend an overall width of the prosthesis. For example, a portion of the posterior wall 12 of the second portion 34 may be inset with the first portion 32 and/or the remainder of the prosthesis 10 in a collapsed state to minimize the overall profile during insertion. A portion of the posterior wall 12 of the second portion 32 may subsequently be moved in a posterior direction, thereby allowing selective expansion and the accompanying support for various tissue sizes and dimensions.

The mechanism for deploying the prosthesis 10 into an expanded state may include, for example, a worm gear linkage, a beveled gear interface, rack and pinion construct, or the like that allows the position of the second portion 34 to be adjusted with respect to the first portion 32. For example, the second portion 34 may include a plurality of gear teeth 36 on a surface thereof. The gear teeth 36 may be disposed on an interior of the prosthesis 10 to avoid pinching or engaging surrounding tissue when the prosthesis is implanted. The gear teeth 36 may be accessible through an opening or instrument engagement feature on the prosthesis. For example, the proximal sidewall 16 may define or include a first instrument engagement feature 38, such as an aperture or passage extending through the sidewall that allows access to the gear teeth 36. Providing for expansion or deployment of the prosthesis 10 through a portion of the proximal sidewall 16 allows a surgeon to continue working through a minimally-invasive, lateral surgical access point through which the prosthesis is initially introduced and positioned, as described below.

The prosthesis 10 may include one or more additional surgical instrument attachment features that allow releasable engagement with and manipulation of the prosthesis into a variety of different positions and/or that facilitate different phases of positioning, deploying, and/or securing the prosthesis into a final position or configuration. For example, the prosthesis may include a second surgical instrument attachment feature 40 to facilitate general positioning of the prosthesis 10. The second attachment feature 40 may include, for example, a threaded opening or portion in the proximal sidewall 16 of the prosthesis 10. The prosthesis 10 may also include a third surgical instrument attachment feature 42 that is releasably engageable with an instrument to aid in either rotating or securing the rotational position of the prosthesis, as well as securing a relative position between the first and second portions of the prosthesis 10. For example, the third instrument attachment feature 42 may include an aperture in the proximal sidewall 16 that is alignable with any one of a plurality of apertures 44 in the second portion 34 of the prosthesis 10. The plurality of apertures 44 of the second portion 34 that are alignable with the third instrument attachment feature allows the second portion 34 to be selectively deployed into a plurality of selectable, discrete positions with respect to the first portion 32.

The prosthesis 10 may include a locking element 46 that secures the selected state of deployment or expansion. The locking element 46 may include, for example, an elongated pin or body that extends through segments of the first and second portions 32, 34 of the prosthesis to prevent movement between the first and second portions. The locking element may include a plurality of protrusions that engage the gear teeth 36 of the second portion 34, while also statically engaging a segment of the first portion 34. The locking element 46 may be positionable through one or more of the instrument attachment features to take advantage of an existing passageway or access point of the prosthesis, which eliminates the need to expand the surgical access incision or to create additional incisions to complete insertion and/or deployment of the prosthesis. The locking element 46 and/or the prosthesis 10 may also include one or more protrusions, tabs, or other structures that prevent over-insertion of the locking element 46 (e.g., having a portion of the locking element unintentionally extend beyond one or more surfaces or sidewalls of the prosthesis 10), which could result in injury to the surrounding tissue.

Figure 3:
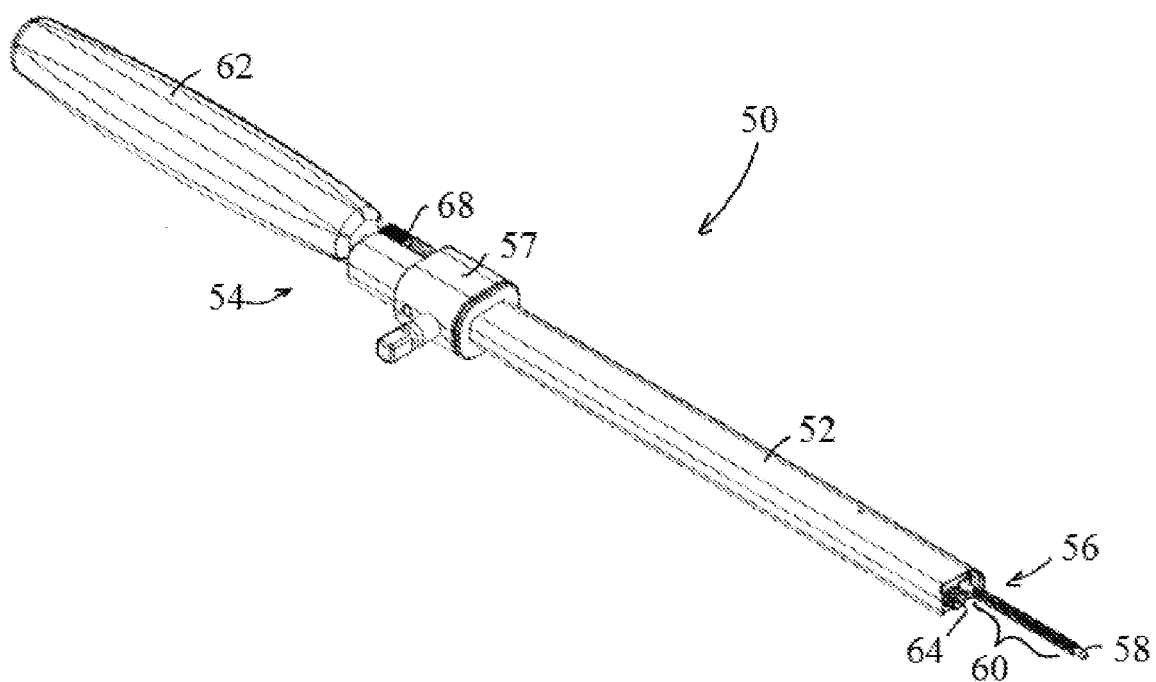
FIG. 3 is an illustration of an example of a surgical instrument in accordance with the present disclosure.
Figure 4:
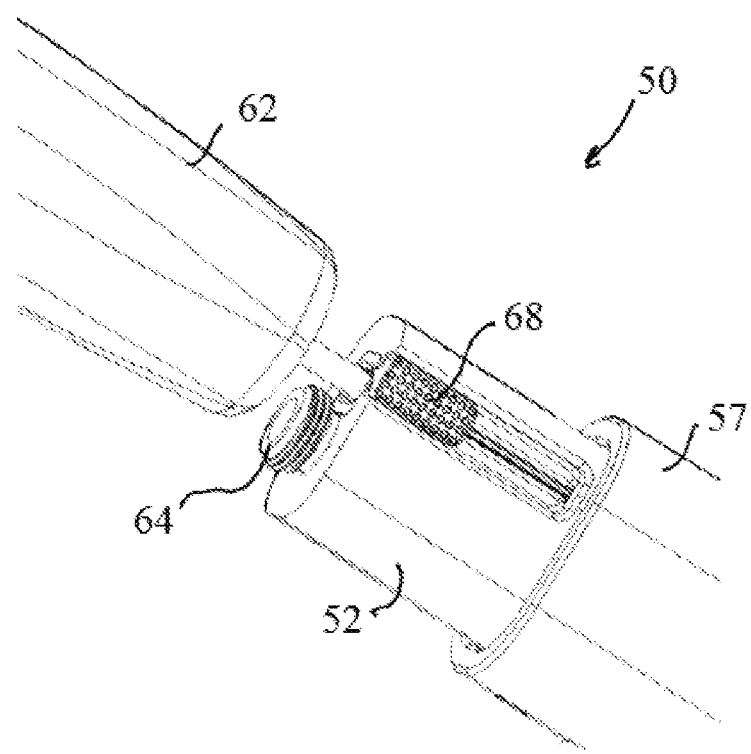
FIG. 4 is an illustration of a proximal portion of the instrument of FIG. 3.
Figure 5:
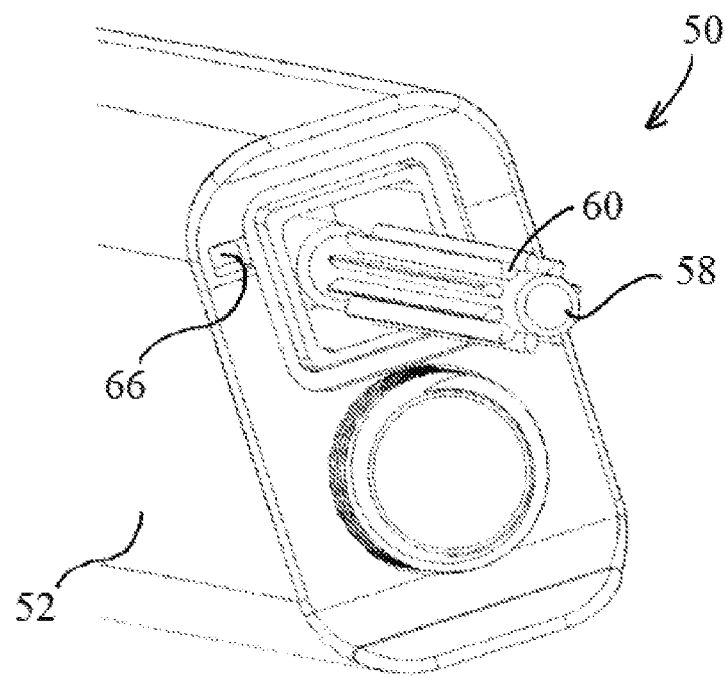
FIG. 5 is an illustration of a distal portion of the instrument of FIG. 3.

Now referring to FIGS. 3-5, an example of a surgical instrument 50 is shown that may be used to position, orient, and adjustably expand the prosthesis 10. The surgical instrument may generally include an elongate body 52 having a proximal portion 54 and a distal portion 56. The proximal portion 54 may include one or more controls or other features operable by a user or surgeon during a medical procedure, while the distal end is adapted and configured to be inserted through an incision or otherwise positionable in proximity to a surgical site, which may include a spinal segment to be treated. The elongate body may define a plurality of lumens or passages therethrough allowing the complementary use of various tools or auxiliary instruments with the surgical instrument 50. The instrument 50 may include a collar 57 to facilitate attachment of the instrument 50 to a table mount or other structure for image-guided alignment with a designated surgical site.

The surgical instrument 50 may include a plurality of prosthesis engagement elements to grasp, rotate, expand, contract, or otherwise manipulate the prosthesis 10. For example, the surgical instrument 50 may include a first prosthesis engagement element 58 that is operable to controllably deploy or expand the prosthesis 10 (or, alternatively, to contract the prosthesis 10). The first prosthesis engagement element 58 may be complementarily matable with the expansion mechanism of the prosthesis 10 at the distal portion 56 of the instrument 50, while being operable or controllable to a user at the proximal portion 54 of the instrument. For example, the first engagement element 58 may include an elongated rod having a plurality of gear teeth 60 engageable with the plurality of gear teeth 36 of the second portion 34 of the prosthesis 10. The first engagement element may also include a handle 62 or other operable means coupled to the proximal portion of the elongate body. Alternatively, the first engagement element 58 may include a rotatable screw or interface engageable to a power-driven tool to facilitate its operation and resulting expansion of the prosthesis 10.

The first engagement element 58 may be movably positionable within the body 52 of the instrument, and one or more instruments or components may be slidably positionable along the length of the body 52 coaxially with the first engagement element 58. For example, the locking element 46 may be passable through an interior of the body 52, and aligned with and/or inserted into the prosthesis 10 at least in part by the first engagement element 58. Alternatively, the first engagement element 58 may be removed from the body 52 of the instrument, and the locking element may be inserted through the passage of the body 52 that the first engagement element was removed from for subsequent insertion into the prosthesis at the distal portion 56 of the instrument 50.

The instrument 50 may also include a second prosthesis engagement element 64 operable to secure the prosthesis 10 to the instrument for positioning, or during deployment. For example, the second engagement element 64 may include a threaded rod or surface that is releasable engageable with the second instrument engagement feature 40 of the prosthesis 10. The threaded portion of the second engagement element 64 may extend from the distal portion 56 of the instrument 50, while also including a segment or portion operable from the proximal portion 54 during a medial procedure.

The instrument 50 may further include a third prosthesis engagement element 66 that is engageable with the prosthesis 10 to facilitate positioning or deployment. For example, the third prosthesis engagement element 66 may include a rod selectively extendable form the distal portion 56 of the instrument 50 and engageable with the third instrument engagement feature 42 of the prosthesis 10. The third engagement element 66 may be coupled to the prosthesis to hold the prosthesis in place and to resist rotation or movement of the prosthesis when engaging or disengaging the other instrument engagement elements from the prosthesis 10. Operation of the third engagement element 66 may include manipulating a slider or actuator 68 coupled to the proximal portion 54 of the instrument 50 that results in the extension or retraction of the engagement element at the distal portion 56 of the instrument 50. The third engagement element 66 may be biased to return to a first position (in which the engagement element 66 may be retracted) without added input to ease the use of the instrument 50.

In a method of exemplary use, the instrument 50 is used to direct the prosthesis 10 into spinal segment between two vertebrae. For example, a patient needing an intervertebral prosthesis may be appropriately prepared for spinal surgery, and an incision may be made to access the diseased or damages portion of the spine requiring treatment. A portion of the tissue in the surgical site may be removed to accommodate introduction of the prosthesis 10. The prosthesis 10 is initially secured to the instrument 50 in a collapsed or un-deployed state. The releasable attachment of the prosthesis may include the engagement of the second prosthesis engagement element (such as threaded rod, for example) to the second instrument engagement feature 40 of the prosthesis 10, which may include a complimenting threaded surface. The prosthesis may then be introduced into the patient and directed towards the surgical site for implantation. The approach for insertion and placement may include a lateral approach. Traditional posterior fusion techniques require the dissection and retraction of back muscles, bones, vessels, ligaments, and nerves; whereas traditional anterior approaches through the abdominal musculature risk injury to major vascular structures such as the aorta and iliac vessels, as well as the very delicate genitourinary structures. Employing a lateral approach allows a surgeon to address spinal pathology from the side of the patient, which can utilize real-time nerve localizing and monitoring techniques, thus minimizing surrounding tissue trauma and maximizing safety and efficacy.

Figure 6:
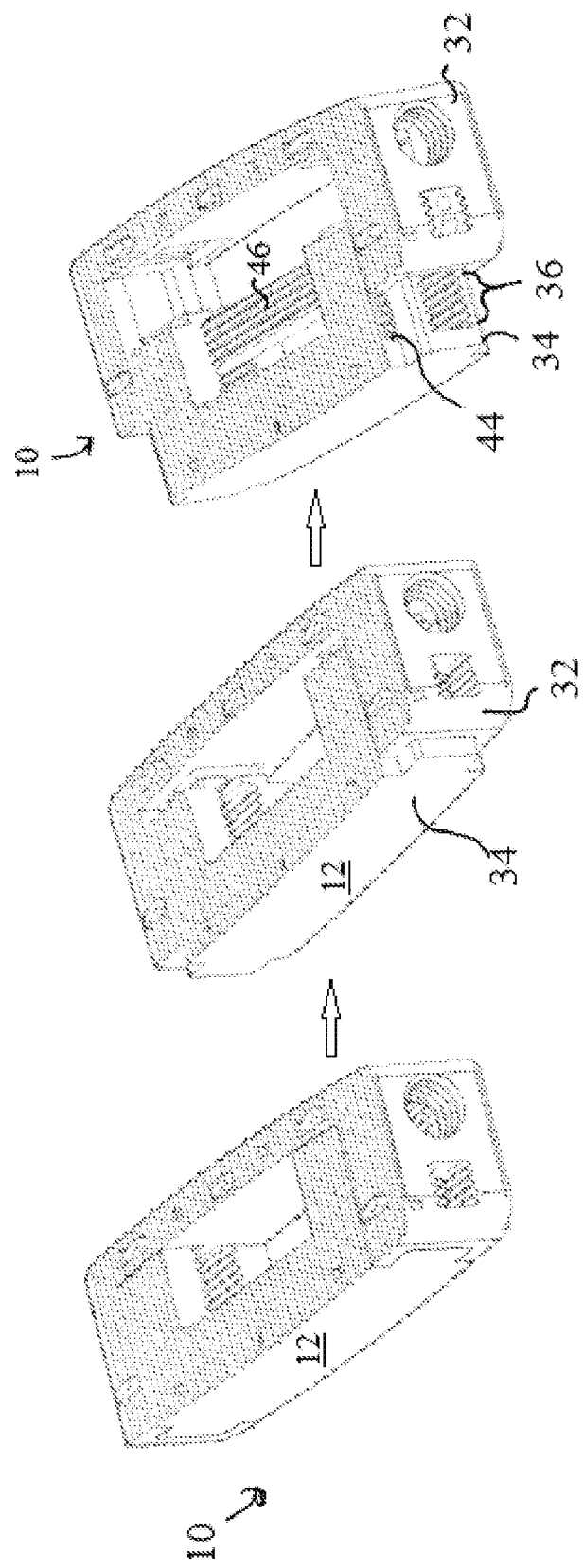
FIG. 6 is an illustration of an expansion or deployment process for the prosthesis shown in FIG. 1.

Once the prosthesis 10 has been positioned within the intervertebral space in a collapsed or un-deployed state, as shown in FIGS. 1-2, the prosthesis 10 can be expanded or deployed. Turning now to FIG. 6 (the instrument 50 has been omitted from these figures), the process of expanding or deploying the prosthesis 10 is illustrated, which involves an extension of the posterior wall 12 away from the remaining body of the prosthesis 10. First, the prosthesis 10 is inserted in a collapsed state without the locking element 46 in place. Once in the desired position, the instrument 50 is used to begin expansion of the prosthesis 10. For example, the gear teeth 60 of the first prosthesis engagement element 58 may be positioned adjacent the gear teeth 36 of the second portion 34 of the prosthesis 10. The first engagement element 58 may then be actuated to move the second portion 34 of the prosthesis 10 away from the first portion 32 of the prosthesis and in a posterior direction. The posterior expansion may provide a range of motion allowing selective expansion and the accompanying support for a wide range of surgical site sizes, and thus patients. For example, the extension may be up to approximately 10 mm from the stationary portion of the prosthesis 10. The amount or length of expansion of the prosthesis 10 may be monitored using one of the markers 30 disposed on the second portion 34 of the prosthesis.

Once the desired expansion has been attained, the relative position of the first and second portions may be temporarily secured using the third engagement element 66 of the instrument 50. For example, the rod of the third engagement element may be extended from the distal portion 56 of the instrument 50 through the third instrument engagement feature 42 of the first portion 32 and into one of the aligned apertures 44 of the second portion 34. The locking element 46 may then be introduced through the instrument 50 and into the first and second portions 32, 34 of the prosthesis to lock the expanded configuration of the prosthesis 10.

Once the locking element 46 is in place, biologic material may be introduced into the cavity 24 of the prosthesis through the instrument and/or through one of the engagement features or through the locking element itself. The addition of tissue biologic materials (e.g., grafts, tissue scaffolding) or pharmaceutical/therapeutic materials within a portion of the prosthesis 10 upon implantation aids in the securement and incorporation of the prosthesis 10 into the surrounding implantation site. The materials may include a collagen fiber reinforced hydroxyapatite matrix, may be concocted in whole or in part of allograft materials, such as bone, connective, and/or soft tissue from appropriate sources. The added materials may also include one or more biological, chemical, and/or pharmaceutical components disposed therein to promote the infusion and incorporation of the materials, and thus the prosthesis, with the surrounding tissue of the implant site. For example, bone morphogenetic proteins may be used to improve the likelihood of creating an osteoinductive or osteoconductive environment post-operatively synergistically with natural biological healing mechanisms. Incorporating these materials into the passages of the prosthesis 10 may decrease complications associated with the exclusive use of allograft or autograft materials, and further eliminate the need to harvest autogenous bone during a particular operation or procedure.

Once the prosthesis is positioned, expanded, and any additional therapeutic material has been introduced, the second prosthesis engagement element 64 of the instrument 50 may be disengaged from the prosthesis. Disengagement of the second prosthesis engagement element 64 may be performed while the third engagement element 66 is still attached to prevent unwanted shifting or movement of the prosthesis. The third engagement element may subsequently be disengaged from the prosthesis as well, and the instrument 50 may be retracted.

Figure 7:
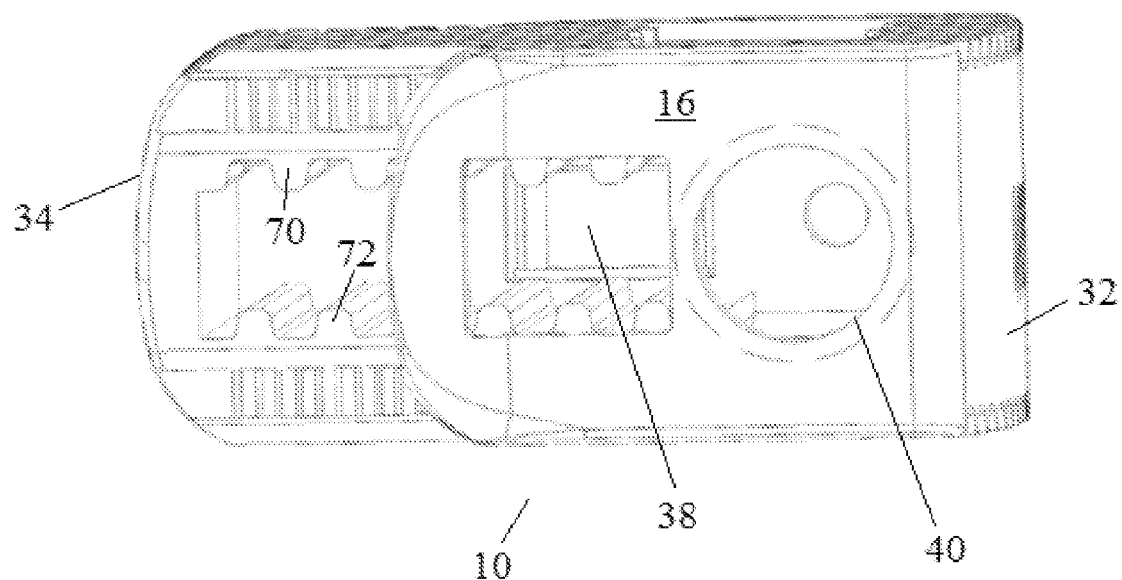
FIG. 7 is a side-view illustration of an example of a spinal prosthesis constructed in accordance with the present disclosure.

Now referring to FIGS. 7-10, additional and/or alternative features of the prosthesis 10 are disclosed. For example, as shown in FIG. 7, the gear teeth 36 of the prosthesis 10 may include a plurality of gear teeth that are out-of-phase and/or not aligned with each other. In the example shown, the gear teeth 36 include a first plurality of gear teeth 70 toward an upper or cranial portion of the second portion 34, and a second plurality of gear teeth 72 toward a lower or caudal portion of the second portion 34, where the first and second pluralities of gear teeth 70,72 are shown out of phase approximately 180° with respect to each other. Misaligning or displacing the relative position of the pluralities of gear teeth 70, 72 allows finer control over the incremental displacement/expansion of the second portion 34 from the first portion 32 of the prosthesis 10 during a procedure. Both the phasing and geometry of the gear teeth 36 (e.g., triangular, square-shaped, or other geometrical cross-sectional tooth shapes) may be varied to achieve the desired displacement and incremental expansion control of the prosthesis 10 when being expanded with the corresponding features of the instrument 50.

Figure 8:
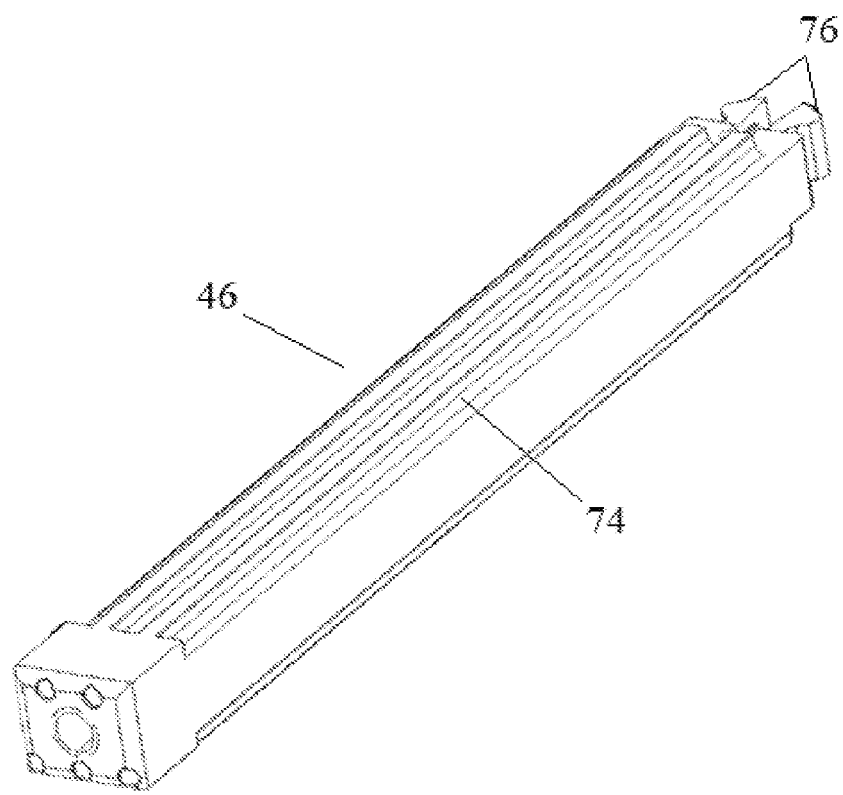
FIG. 8 is a perspective-view illustration of an example of a locking element constructed in accordance with the present disclosure.
Figure 9:
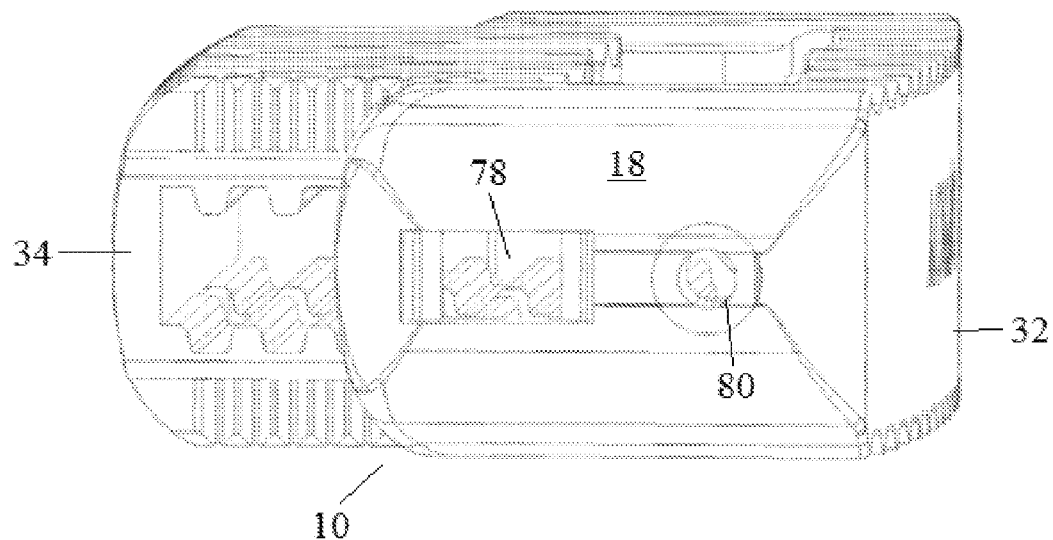
FIG. 9 is an additional side-view illustration of the prosthesis shown in FIG. 7.

Now referring to FIG. 8, an example of the locking element 46 is shown that is engageable with the modified, phase-spaced gear teeth 36 of the prosthesis 10 shown in FIG. 7. As shown, the locking element 46 includes teeth and depressions 74 on its surfaces complimentary to and engageable with the gear teeth 36. The locking element may include orientation markings (not shown) to aid a surgeon on orienting the locking element 46 properly with the gear teeth 36 of the prosthesis 10. The locking element 46 may also include a retention feature 76 that securely engages the distal sidewall 18 of the prosthesis 10 upon insertion of the locking element 46. In the illustrated example, the retention feature 76 includes a two-pronged clip at the distal end of the locking element 46. The two-pronged clip is compressible to pass through a similarly sized opening in the distal sidewall 18 (e.g., opening 78 shown in FIG. 9), and upon passing through the opening, the prongs expand or resiliently spring back into their original size and position to secure the locking element 46 in place and, as described above, secure the selected expansion configuration of the prosthesis 10.

The prosthesis 10 may include one or more features to further secure a selected expansion or displacement configuration of the prosthesis during a procedure when the locking element 46 and/or various features of the instrument 50 are being engaged, disengaged and/or transitioned with respect to the various engagement features of the prosthesis 10. For example, the distal sidewall 18 may define an aperture 80 that is matable and/or engageable with a portion of the instrument 50, such as the second engagement element 64, to provide increased rigidity and reinforcement along substantially an entire length of the prosthesis 10 during an implantation procedure and prevents unwanted flexing or displacement of the prosthesis 10. The second engagement element 64 may include an extended portion or increased length (not shown) in order to traverse the length of the prosthesis 10 and engage the aperture 80, which may include threading or other mechanical features to releasably attach to the instrument 50.

Figure 10:
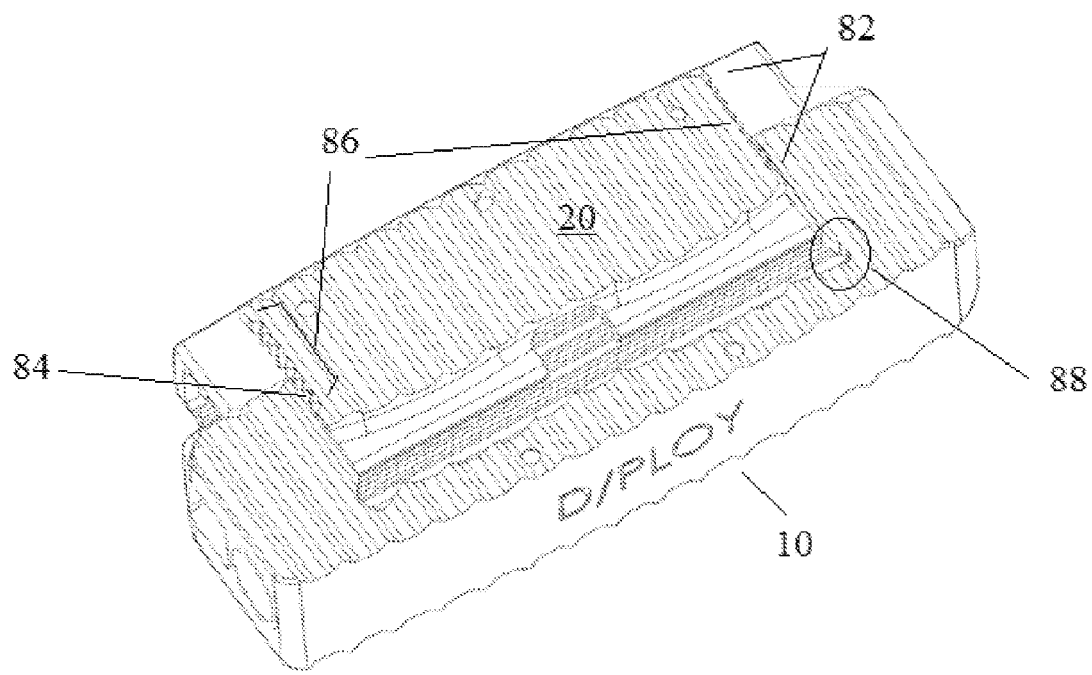
FIG. 10 is a perspective-view illustration of the prosthesis shown in FIG. 7.

The prosthesis 10 may further include a displacement or expansion indexing feature that provides tactile and/or audible feedback to the surgeon during the expansion of the prosthesis 10. For example, as shown in FIG. 10, the prosthesis 10 may include one or more displacement indicators 82 that provides tactile and audible feedback to a surgeon as the second portion 34 of the prosthesis is displaced from the first portion of the prosthesis 32. In the illustrated example, displacement indicators 82 are located on a cranial surface of the prosthesis 10 in proximity to each of the proximal and distal sidewalls 16, 18. Each displacement indicator 82 includes a protruding segment or tooth 84 extending from or otherwise coupled to the first portion 32 of the prosthesis. The protruding segment 84 is aligned with a plurality of complimentary depressions 86 formed in or otherwise coupled to the second portion 34 of the prosthesis 10. When the second portion 34 is displaced or expanded away from the first portion 32 of the prosthesis, the protruding segment 84 is displaced incrementally and successively along the plurality of complimentary depressions 86 to provide a tactile and audible "click" that provides an indication and reference to the surgeon for the progressive expansion of the prosthesis 10. A range of sizes and shapes of the protruding segment 84 and the depressions 86 may be available in a plurality of prostheses 10 to allow a surgeon to select an incremental indicator with a known measurement (e.g., every "click" or change in position equates to a 1 mm expansion/displacement; in another model or size, a "click" may equate to 1.5 mm in expansion/displacement) suitable for a particular patient.

The prosthesis 10 may include one or more stress or strain relief features or geometric configurations to allow the prosthesis to flex sufficiently to allow the displacement indicator(s) 74 to operate. For example, as shown in FIG. 10, the first portion 32 of the prosthesis includes curved "cut-outs" 88 at the corners of the cavity 24 to allow the first portion 32 to flex or bow, thereby providing sufficient space for the protruding segment 84 to transition along the incremental, successive depressions 86 without damaging the prosthesis 10 or otherwise compromising its structural integrity.

The displacement indicator 82 also provides resistance to unintentional or inadvertent expansion or collapse of the prosthesis 10. For example, the protruding segment 84 provides a ratchet-lock-type mechanism that can resist compression or exerted force from surrounding tissue that could otherwise cause the prosthesis to collapse or deviate from the expansion position selected by the surgeon from the plurality of discrete, incremental expansion positions offered by the plurality of depressions 86 mating with the protruding segment 84.

Of note, although features of the prosthesis 10 have been described as "proximal," "distal," "anterior," "posterior," etc., such terms are used only for ease of explanation and do not limit the orientation or placement of the prosthesis in a given surgical site or cavity. For example, the prosthesis 10 may be inserted or oriented such that the prosthesis 10 is expanded in a posterior direction, in an anterior direction, in a lateral direction, or in a medial direction with respect to the patient.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. An expandable spinal prosthesis, comprising:
   a first surface and a second surface opposite the first surface, and a prosthesis height defined therebetween;
   a first wall extending between the first and second surfaces;
   a second wall extending between the first and second surfaces, the second wall located opposite the first wall;
   a first sidewall extending from the first wall to the second wall, wherein the first sidewall defines an opening therethrough; and
   a second sidewall extending from the first wall to the second wall, wherein the first wall, first sidewall and second sidewall form a unitary first portion;
   wherein at least a portion of the second wall forms a second portion movable relative to the first portion to extend an overall width of the prosthesis body; and
   wherein the second portion includes a first plurality of gear teeth and a second plurality of gear teeth positioned out-of-phase with respect to the first plurality of gear teeth, and wherein the first and second pluralities of gear teeth are accessible through the opening in the first sidewall.

2. The expandable spinal prosthesis according to claim 1, wherein the position of the second portion is configured to be adjusted relative to the first portion using an external tool engaged with the first and second pluralities of gear teeth.

3. The expandable spinal prosthesis according to claim 1, wherein the second portion is securable in a plurality of discrete positions with respect to the first portion.

4. The expandable spinal prosthesis according to claim 1, further comprising a displacement indicator coupled to at least one of the first and second portions, wherein the displacement indicator provides at least one of a tactile and audible response to the movement of the second portion relative to the first portion.

5. The expandable spinal prosthesis according to claim 4, wherein the displacement indicator includes a protruding segment coupled to the first portion that is engageable with a plurality of depressions defined by the second portion.

6. The expandable spinal prosthesis according to claim 5, wherein the second portion defines at least one strain relief allowing the second portion to flex.

7. The expandable spinal prosthesis according to claim 6, wherein the at least one strain relief includes a curvilinear recess in at least one of the first and second surfaces.

8. The expandable spinal prosthesis according to claim 1, further comprising a locking element positionable through the opening in the first sidewall and engageable with the first and second pluralities of gear teeth to prevent movement between the first and second portions.

9. The expandable spinal prosthesis according to claim 8, wherein the locking element includes a retention feature configured to resist movement of the locking element with respect to the first portion of the prosthesis.

10. The expandable spinal prosthesis according to claim 9, wherein the retention feature includes a multi-prong clip configured to releasably engage an aperture defined by the second sidewall.

11. The expandable spinal prosthesis according to claim 1, wherein the first and second portions define a cavity therebetween, the cavity extending through the height of the prosthesis from the first surface to the second surface.

12. The expandable spinal prosthesis according to claim 11, wherein the cavity defines a substantially rectangular-shaped cross section.

13. The expandable spinal prosthesis according to claim 1, further comprising a radiopaque marker coupled to at least one of the first and second portions.

14. The expandable spinal prosthesis according to claim 1, wherein the first sidewall defines a first surgical instrument engagement feature, and the second sidewall defines an aperture coaxial with the first surgical instrument engagement feature.

15. The expandable spinal prosthesis according to claim 14, wherein the first surgical instrument engagement feature includes a threaded surface.

16. A method of implanting a spinal prosthesis within a patient, comprising:
    positioning a spinal prosthesis according to claim 1 within an intervertebral space; and
    moving the second portion in a substantially posterior direction away from the first portion to increase a width of the prosthesis in an anterior-posterior direction.

17. The method of claim 16, further comprising securing the position of the second portion relative to the first portion.

18. The method of claim 16, wherein moving the second portion in a substantially posterior direction is accomplished at least in part by mechanically actuating the first and second pluralities of gear teeth.

19. The method of claim 16, further comprising introducing a biologic material into a cavity defined by the prosthesis.

20. The method of claim 16, wherein positioning the spinal prosthesis includes directing the prosthesis into the intervertebral space in a substantially lateral-to-medial direction.

* * * * *